US008329734B2

(12) United States Patent
Aung-Din

(10) Patent No.: US 8,329,734 B2
(45) Date of Patent: *Dec. 11, 2012

(54) TOPICAL THERAPY FOR MIGRAINE

(75) Inventor: Ronald Aung-Din, Sarasota, FL (US)

(73) Assignee: AFGIN Pharma LLC, Sarasota, FL (US)

( * ) Notice: Subject to any disclaimer, the term of this patent is extended or adjusted under 35 U.S.C. 154(b) by 163 days.

This patent is subject to a terminal disclaimer.

(21) Appl. No.: 12/460,966

(22) Filed: Jul. 27, 2009

(65) Prior Publication Data

US 2011/0021596 A1    Jan. 27, 2011

(51) Int. Cl.
A61K 31/41    (2006.01)
A61K 31/255   (2006.01)
A61L 15/16    (2006.01)
(52) U.S. Cl. .................... 514/359; 514/517; 424/444
(58) Field of Classification Search .................. 514/359, 514/517; 424/444
See application file for complete search history.

(56) References Cited

U.S. PATENT DOCUMENTS

| | | | |
|---|---|---|---|
| 3,598,122 A | 8/1971 | Zaffaroni | 128/268 |
| 3,797,494 A | 3/1974 | Zaffaroni | 128/268 |
| 4,144,317 A | 3/1979 | Higuchi et al. | 424/21 |
| 4,201,211 A | 5/1980 | Chandrasekaran et al. | 128/268 |
| 4,262,003 A | 4/1981 | Urquhart et al. | 424/267 |
| 4,379,454 A | 4/1983 | Campbell et al. | 604/897 |
| 4,511,563 A | 4/1985 | Schmolka | 514/162 |
| 4,588,580 A | 5/1986 | Gale et al. | 424/21 |
| 4,767,619 A | 8/1988 | Murray | 424/78 |
| 4,806,341 A | 2/1989 | Chien et al. | 424/448 |
| 4,816,470 A | 3/1989 | Dowle et al. | 514/415 |
| 4,820,720 A | 4/1989 | Sanders et al. | 514/356 |
| 4,861,760 A | 8/1989 | Mazuel et al. | 514/54 |
| 4,883,660 A | 11/1989 | Blackman et al. | 424/78 |
| 4,916,132 A | 4/1990 | Seibel | 514/250 |
| 5,016,652 A | 5/1991 | Rose et al. | 131/270 |
| 5,026,556 A | 6/1991 | Drust et al. | 424/449 |
| 5,037,845 A | 8/1991 | Oxford | 514/415 |
| 5,053,227 A | 10/1991 | Chiang et al. | 424/448 |
| 5,069,909 A | 12/1991 | Sharma et al. | 424/449 |
| 5,307,953 A | 5/1994 | Regan | 222/82 |
| 5,318,780 A | 6/1994 | Viegas et al. | 424/427 |
| 5,364,628 A | 11/1994 | Kissel et al. | 424/448 |
| 5,466,699 A | 11/1995 | Robertson et al. | 514/323 |
| 5,521,196 A | 5/1996 | Audia et al. | 514/323 |
| 5,545,644 A | 8/1996 | Macor et al. | 514/323 |
| 5,554,639 A | 9/1996 | Craig et al. | 514/415 |
| 5,698,571 A | 12/1997 | Audia et al. | 514/323 |
| 5,705,520 A | 1/1998 | Craig et al. | 514/415 |
| 5,719,197 A | 2/1998 | Kanios et al. | 514/772.6 |
| 5,807,571 A | 9/1998 | List | 424/449 |
| 5,837,289 A | 11/1998 | Grasela et al. | 424/484 |
| 5,855,907 A | 1/1999 | Peyman | 424/434 |
| 5,863,559 A | 1/1999 | Phillips et al. | 424/480 |
| 5,863,935 A | 1/1999 | Robertson et al. | 514/414 |
| 5,872,145 A | 2/1999 | Plachetka | 514/415 |
| 6,020,001 A | 2/2000 | Phillips et al. | 424/480 |
| 6,060,499 A | 5/2000 | Plachetka | 514/415 |
| 6,103,266 A | 8/2000 | Tapolsky et al. | 424/484 |
| 6,197,331 B1 | 3/2001 | Lerner et al. | 424/448 |
| 6,368,627 B1 | 4/2002 | Phillips et al. | 424/480 |
| 6,383,471 B1 | 5/2002 | Chen et al. | 424/45 |
| 6,384,034 B2 | 5/2002 | Simitchieva et al. | 514/252 |
| 6,455,557 B1 | 9/2002 | Pellegrini et al. | 514/362 |

FOREIGN PATENT DOCUMENTS

| | | |
|---|---|---|
| EP | 0303507 | 2/1989 |
| EP | 0500086 | 8/1992 |
| EP | 0636623 | 2/1995 |
| EP | 0705600 | 10/1996 |
| WO | 9118897 | 12/1991 |
| WO | 9206973 | 4/1992 |
| WO | 9426270 | 1/1994 |
| WO | 9505137 | 2/1995 |
| WO | 03024456 | 3/2003 |
| WO | 03032983 | 4/2003 |
| WO | 2004112723 | 12/2004 |

OTHER PUBLICATIONS

Messlinger, K; Hotta, H.; Pawlak, M.; Schmidt, R.F., Effects of the 5-HT1 receptor agonists, sumatriptan and CP 93,129, on dural arterial flow in the rat, Eur J Pharmacol, vol. 332 No. 2, Aug. 6, 1997 pp. 173-181.

Piovesan, et al., "Referred Pain After Painful Stimulation of the Greater Occipital Nerve in Humans: Evidence of Convergence of Cervical Afferences on Trigeminal Nuclei", Cephalalgia, 2001, 21, 107-109.

Rougier, et al. In vivo percutaneous penetration of some organic compounds related to anatomic site in humans; predictive assessment by the stripping method, J. Pharmac. Sci., vol. 76, No., Jun. 1987, pp. 451-454.

Goodman & Gilman, The Pharmacological Basis of Therapeutics, Ninth Edition, (1996), Chapter 21, Peroutka, Drugs Effective in the Therapy of Migraine, pp. 487-502.

Chepyala et al., Treatment of Cyclic Vomiting Syndrome, Current Treatment Options in Gastroerology, 2007, 10: abstract only.

Remington's Pharmaceutical Sciences, 15$^{th}$ edition, 1975, Mack Publishing Co. p. 1529.

Methods Find Exp Clin Pharmacol 2002, 24(6): 371-391—Gateways to Clinical Trials—Jul.-Aug. 2002 M. Bayes, X. Rabasseda, J.R. Prous.

Schwarz, et al., Postdural Puncture Headache: Diagnosis, Prevention and Therapy Schmerz, vol. 13, No. 5, 1999—pp. 332-340.

Office Action dated Aug. 1, 2007 issued in corresponding U.S. Appl. No. 10/163,234.

Applicant's Response to Office Action dated Jan. 19, 2007 issued in corresponding U.S. Appl. No. 10/163,234.

Office Action dated Sep. 21, 2006 issued in corresponding U.S. Appl. No. 10/163,234.

Applicant's Response to Office Action dated Mar. 15, 2006 issued in corresponding U.S. Appl. No. 10/163,234.

Office Action dated Nov. 17, 2005 issued in corresponding U.S. Appl. No. 10/163,234.

Applicant's Response to Office Action dated Aug. 18, 2005 issued in corresponding U.S. Appl. No. 10/163,234.

(Continued)

Primary Examiner — Renee Claytor
(74) Attorney, Agent, or Firm — Davidson, Davidson & Kappel, LLC

(57) ABSTRACT

The invention is directed to formulations and methods of treating a migraine and/or cluster headache with a serotonin agonist, pharmaceutically acceptable salt thereof, or derivative thereof.

17 Claims, No Drawings

OTHER PUBLICATIONS

Office Action dated Apr. 18, 2005 issued in corresponding U.S. Appl. No. 10/163,234.

Aung-Din, Ronald, Transdermal Sumatriptan: A Novel Dosage Form Efficacious in the Treatment of Acute Migraine, Headache: The Journal of Head and Face Pain, vol. 45, No. 5, May 2002.

Aung-Din, Ronald, Transdermal Sumatriptan in Clinical Practice: The Experience of 42 Patients with Acute Migraine in an Outpatient Setting, Headache: The Journal of Head and Face Pain, vol. 43, No. 5, May 2003.

Aung-Din, Ronald and Kinnard, Fred, Topical Tizanidine (Zanaflex) Gel Effective in Migraine and Tension-Type Headache, Headache: The Journal of Head and Face Pain, vol. 44, No. 5, May 2004.

Norton, Patrice G.W., Transdermal Sumatriptan May Relieve Migraines, Internal Medicine News, vol. 36, Issue 19, p. 14, Oct. 1, 2003.

International Search Report dated Nov. 5, 2002 issued in corresponding International Patent Application No. PCT/US02/17585.

European Search Report dated Oct. 3, 2006 issued in corresponding European Patent Application No. 02 739 657.1-2123.

International Search Report dated Jun. 6, 2005 issued in corresponding International Patent Application No. PCT/US04/19816.

Applicant's Response to Office Action dated May 19, 2009 issued in corresponding U.S. Appl. No. 11/999,093.

Office Action dated Mar. 19, 2009 issued in corresponding U.S. Appl. No. 11/999,093.

Applicant's Response to Office Action dated Dec. 12, 2008 issued in corresponding U.S. Appl. No. 11/999,093.

Applicant's Response to Office Action dated Oct. 21, 2008 issued in corresponding U.S. Appl. No. 11/999,093.

Office Action dated Jun. 23, 2008 issued in corresponding U.S. Appl. No. 11/999,093.

TOPICAL THERAPY FOR MIGRAINE

Applicant hereby claims priority of U.S. patent application Ser. No. 11/999,093 filed Dec. 3, 2007; U.S. patent application Ser. No. 10/163,234, filed on Jun. 5, 2002, which claims the benefit of U.S. Provisional Patent Application No. 60/296,286, filed Jun. 5, 2001, the disclosures of which are incorporated herein by reference in their entireties for all purposes.

BACKGROUND OF THE INVENTION

Migraine headaches are a debilitating condition in which some 53 million persons per year suffer acute pain. Frequently, migraine is accompanied by sickness and vomiting and a sensitivity to light and noise.

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, Serotonin in Mental Abnormalities, 1: 41 (1978); H. W. M. Steinbusch, HANDBOOK OF CHEMICAL NEUROANATOMY, Volume 3, Part 11, 68 (1984); N. E. Anden, et al., Acta Physiologica Scandinavia, 67: 313 (1966). These studies have been complemented by biochemical evidence that indicates large concentrations of 5-HT exist in the brain and spinal cord. H. W. M. Steinbusch, supra.

Serotonin (5-hydroxytryptamine, 5-HT) is said to play a key role in regulating the vascular tone, and serotonin deficiency is said to result in a vasodilatation causing the migrainous headache. The onset of action is effected via $5-HT_1$-receptors in the region of the vascular walls of cerebral arteries.

Accordingly, in the last few years, the chemical structure of serotonin has been modified in various manners, resulting in changes of the pharmacological properties. For example, indole derivatives were synthesized which cause the cerebral vessels to be selectively tonizised (contracted) combined with a rapid improvement of the symptoms. These are so-called serotonin agonists having a particular affinity for $5-HT_1$-receptors.

The class of serotonin agonists having a particular affinity for $5-HT_1$ receptors is typified, for example, by sumatriptan, zolmitriptan, naratriptan, and rizatriptan to name a few. Oral bioavailability is an important factor in the efficacy of a drug and one that may account for consistency of response with repeated use. Sumatriptan tablets have a low oral bioavailability (14%). All of the second-generation triptans have improved bioavailability (rizatriptan and zolmitriptan, 40-45%; naratriptan, close to 70%). Sumatriptan, rizatriptan, and zolmitriptan are metabolized by the MAO system. All of these compounds, however, have some adverse effects which require supervised administration at efficacious doses. PHYSICIAN'S DESK REFERENCE, (48th ed., 1994).

SUMMARY OF THE INVENTION

It is an object of the present invention to provide a method for the treatment of migraines in humans via the topical administration of a serotonin agonist.

It is an object of certain embodiments of the present invention to provide a topical therapeutic formulation for the systemic and/or regional administration of a compound having serotonin agonist activity.

It is an object of certain embodiments of the present invention to provide a topical therapeutic formulation and method for the regional administration of a compound having serotonin agonist activity.

It is an object of certain embodiments of the present invention to provide a more rapid therapeutic effect than previous routes of administration of serotonin agonist.

The above objects and others are attained by virtue of the present invention, which is directed in part to a method of treating a migraine and/or cluster headache via the topical administration and delivery of a therapeutically effective amount of a serotonin agonist to a human in need of treatment thereof.

In certain embodiments, the present invention is directed to a method of treating a migraine and/or cluster headache comprising applying a serotonin agonist to the headache region of a human patient in an effective amount to provide relief of a migraine and/or cluster headache which is occurring or imminent in the human patient.

In certain embodiments, the present invention is directed to a unit dose of a serotonin agonist for topical administration and delivery of the serotonin agonist to a human in need of treatment thereof.

In certain preferred embodiments, the serotonin agonist is in a topical formulation. In certain other preferred embodiments, the serotonin agonist is in a transdermal therapeutic system. Preferably the topical formulation or transdermal therapeutic system is applied to a predetermined area of skin to deliver the serotonin agonist to a human.

In certain preferred embodiments, the formulations of the present invention provide an effective dose of the serotonin agonist at the application site, which is quickly absorbed. Most preferably the formulations of the present invention are immediate releasing formulations, such that a therapeutically effective amount of the serotonin agonist is available for rapid absorption. The formulations of the present invention preferably are suitable for the treatment of an acute migraine attack.

The topical formulation comprising the serotonin agonist or transdermal therapeutic system comprising the serotonin agonist is preferably applied to the posterior cervical region of the human experiencing or about to experience a migraine and/or cluster headache. Most preferably, the topical formulation or transdermal therapeutic system is applied to the back of the neck, preferably in close proximity to or on the area of skin above the brain stem.

In certain preferred embodiments the symptoms of the migraine or cluster headache are relieved within about 2 hours, preferably within about 5 minutes to about 2 hours, within about 5 minutes to about 1 hour and most preferably within about 5 minutes to about 30 minutes after application of the serotonin agonist. In certain preferred embodiments, the formulations of the present invention provide migraine or cluster headache relief within from less than 1 minute to about 2 hours, about 1 minute to about 2 hours, preferably in about 1 minute to about 15 minutes.

In certain embodiments, the present invention is directed towards a unit dose of a topical formulation for treating a migraine or cluster headache comprising a serotonin agonist incorporated into a pharmaceutically acceptable vehicle for topical administration onto the skin of a human patient; said unit dose providing said serotonin agonist in a form which is immediately absorbable when said unit dose is applied onto human skin; said serotonin agonist comprising from about 0.5 to about 200 mg of sumatriptan, by weight based on the succinate salt, or a therapeutic equivalent dose of another topically absorbable pharmaceutically acceptable serotonin agonist; and said unit dose providing relief from a migraine or cluster headache within about 2 hours after topical administration to said human patient.

In certain embodiments, the present invention is directed to a unit dose of a topical formulation for treating a migraine or cluster headache comprising a serotonin agonist; and a pharmaceutically acceptable vehicle; said unit dose containing from about 0.5 mg to about 200 mg of said serotonin agonist, and providing pain relief in at least 50 percent of a population of patients experiencing a migraine or cluster headache, in a time period within about 2 hours after application of the unit dose to the headache region.

In certain embodiments, the present invention is further directed to a method of reducing side effects of a serotonin agonist administered in migraine or cluster headache therapy comprising topically administering a therapeutically effective amount of a serotonin agonist to the headache region of a patient in need of migraine or cluster headache therapy.

In certain embodiments of the present invention, the formulation comprising the serotonin agonist, further comprises one or more ingredients selected from the group consisting of ethoxydiglycol, water, glycerine, $C_{12-15}$alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, vitis vinifera (grape) seed extract, triticum vulgare (wheat) germ oil, retinyl palmitate (vitamin A palmitate), ascorbyl palmitate (vitamin C palmitate), prolipo multi-emulsion liposomic system, tetrasodium EDTA, phenoxyethanol, and sodium hydroxymethylglycinate.

In certain embodiments, the methods of the present invention further include applying an additional dose of a serotonin agonist to the headache region about 15 minutes to about 3 hours after the first application of a serotonin agonist, preferably 30 minutes to about 2 hours after the first application of a serotonin agonist, and most preferably from about 30 minutes to about 1 hour after the first application of a serotonin agonist. This embodiment is considered particularly useful when the first application does not alleviate the symptoms of the migraine.

In certain preferred embodiments, the formulations of the present invention are provided in a metered dose device. Preferably the metered dose device provides multiple unit doses of the topical preparation. Certain metered dose devices include, for example and without limitation, a syringe without a needle (e.g., a tuberculin syringe without needle, a dropper, a metered dose spray device, metered tube, and the like. Preferably the metered dose device includes an actuator capable of being actuated to dispense single unit doses comprising the serotonin agonist from the device.

In certain embodiments, the present invention is further directed towards a method of manufacturing the formulations described herein.

For purposes of the present invention, a "topical formulation" includes, for example, ointments, creams, lotions, pastes, gels, foams, viscous liquids, semisolids, etc., which releases one or more drugs at a predetermined rate over a defined period of time to a defined site of application.

For purposes of the present invention, a "transdermal therapeutic system" is defined as a drug-containing device (including e.g., patch, disc, etc.) which releases one or more drugs at a predetermined rate over a defined period of time to a defined site of application.

For purposes of the present invention, "transdermal" delivery is the delivery by passage of a drug through the skin and into the bloodstream.

For purposes of the present invention the term "immediate release" means that the serotonin agonist is available for immediate absorption (e.g., available within 0 to about 5 minutes) upon application of the formulation. This is in contrast to a delayed or prolonged absorption which typically results from, e.g., a transdermal therapeutic device).

For purposes of the present invention "therapeutically effective" or "effective" amount is meant to be a nontoxic but sufficient amount of a compound to provide the desired therapeutic effect, e.g., avoidance of the onset of a migraine and or increased alleviation of the migraine and/or cluster headache. In the present case, for example, it is the dose of serotonin agonist which will be effective in relieving symptoms of the migraine or cluster headache. An "effective" amount of a permeation enhancer as used herein, for example, means an amount that will provide the desired increase in skin permeability and, correspondingly, the desired depth of penetration, rate of administration, and amount of drug to be delivered.

For purposes of the present invention, the term "delivers" when used with respect to the topical formulation or transdermal therapeutic system means that the formulation or system provides a mean relative release rate or flux of the drug out of the formulation or system and through the skin of the patient.

By "predetermined area of skin" is intended a defined area of intact unbroken living skin. In certain embodiments of the present invention, the predetermined area will be in the range of about 1 $cm^2$ to about 100 $cm^2$, preferably in the range of about 10 $cm^2$ to about 100 $cm^2$, more preferably in the range of about 20 $cm^2$ to about 60 $cm^2$. However, it will be appreciated by those skilled in the art of topical delivery that the area of skin through which drug is administered may vary significantly, depending on the formulation, dose, the application of the formulation, and the like.

"Penetration enhancement" or "permeation enhancement" for purposes of the present invention relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus.

For purposes of the present invention, the "headache region" is defined as the skin region of the head and/or neck above which a patient feels a migraine or cluster headache pain is occurring or is imminent. Typically the headache region includes, for example, the frontotemporal region and/or upper posterior cervical area on the side of the headache. Preferably the headache region includes the posterior cervical area in close proximity to the brain stem. Preferably this area is a relatively hairless area of the patient's head and/or neck.

DETAILED DESCRIPTION

Sickness and vomiting typically occurring in migraine make an oral application of the active substance for migraine treatment difficult. Therefore, the administration by the topical administration of a serotonin agonist may offer considerable advantages.

Certain other advantages of topical administration may include increased efficiency by avoiding the first-pass effect of the liver, avoiding discomfort and risks of an intravenous treatment, avoiding side effects in the region of the gastrointestinal tract in the case of oral medication, and good patient acceptance. Absorption peaks involving the risk of systemic side effects may also be avoided.

In the prior art, there have been previous attempts to provide for a more efficacious and safe treatment using serotonin agonists specific for the treatment of 5-HT$_1$ receptor subtype.

For Example, U.S. Pat. No. 5,863,935 to Robertson et al. describes certain compounds having "5-HT$_1$-like" receptor agonist properties and their administration in a number of ways, including topical or intranasal application.

Additionally, U.S. Pat. No. 5,805,571 to List, describes a transdermal therapeutic system for the systemic administration of active substances wherein at least one of the active substances listed is a serotonin agonist of the group comprising indole derivatives. Typically, transdermal systems are not used in acute situations because they do not provide an immediate effect, but rather provide prophylaxis or prolonged effect. Transdermal systems such as that described in the '571 patent to List require a period of time for the drug to pass through a barrier layer and onto/into the skin which may take e.g., a substantial period of time until the dose of drug that is absorbed is sufficient to alleviate the pain associated with the headache.

The above-mentioned patents do not suggest the application of the topical formulation or transdermal therapeutic system on the skin above the site of the migraine or cluster headache attack. Typically the site of administration of transdermal delivery systems have been selected at various locations such as on the chest, on the arm, on the genitalia, or on the thigh for various reasons such as desired skin permeability to an agent, convenience or cosmetic reasons. According to the present invention the topical formulation is preferably applied to the headache region for the local (e.g., regional) and systemic administration of agents to the migraine or cluster headache area and in certain embodiments results in lower serum levels necessary to provide a therapeutic effect than that reported in the prior art.

This method and the formulations described herein allow for the headache to be treated much faster and more effectively than such prior art modes of administration. For example, it is contemplated that a patient experiencing a migraine or cluster headache, or who perceives that such a headache is imminent, can apply the dose of serotonin agonist to the skin at that site and experience relief within, e.g., from about 2 hours, preferably within about 5 minutes to about 2 hours, within about 5 minutes to about 1 hour, about 5 minutes to about 30 minutes. In a most preferred embodiments, relief is experienced within from less than 1 minute to about 2 hours, from less than 1 minute to about 30 minutes, or from less than 1 minute to about 15 minutes after application of the serotonin agonist. The method of the invention further contemplates that if the dose does not completely alleviate the headache, that a second dose may be applied within about 3 hours, preferably within about 15 minutes to about 3 hours, within about 30 minutes to about 2 hours, and most preferably within about 30 minutes to about 1 hour after the first application.

By the methods of the present invention, a substantial percentage of patients experience relief within a relatively short period of time after application. For example, as demonstrated in at least one study described herein, more than 50 percent of the patients experienced pain relief within one hour of the application of the dose of serotonin agonist to the headache region. In certain preferred embodiments, more than 70 percent, most preferably more than 80 percent, of the patients experienced pain relief.

In certain embodiments of the present invention, the method of treating a human patient suffering from migraine or cluster headache comprises applying a topical formulation which comprises a serotonin agonist, as described herein, to the headache region, such that the topical formulation delivers an amount of serotonin agonist which is therapeutically effective. Preferably the topical formulation contains a unit dose of the serotonin agonist that provides relief of a migraine and/or cluster headache. In certain embodiments, the present invention provides a method of treating an imminent migraine attack in a patient comprising topically administering a serotonin agonist to the patient in need of such treatment.

The methods of the present invention may also, if desired, involve pre-treatment of the skin with an enhancer to increase the permeability of the skin to the applied drug. The methods of the present invention may include pre-treatment or "prepping" of the skin area with a substance that opens up the skin pores. Additionally, the methods of the present invention may include, if desired, pre-treatment or "prepping" of the skin with an alcohol swab or the like to rid the area of dirt, makeup, oil, and the like, prior to application of the drug.

In certain embodiments, the topical formulation of the present invention comprises a serotonin agonist in an amount which is therapeutically effective when administered topically at the headache region, but which provides a plasma concentration which is subtherapeutic if orally administered.

In certain embodiments, by applying the formulation of the present invention comprising a dose of serotonin agonist at the headache region of the migraine or cluster headache, it may be possible for the use of lower doses of drug or faster relief of the headache than if applied to the trunk or limbs of a human patient, and the lower plasma levels of drug which result from lower doses may thereby reduce unwanted side effects of the serotonin agonist. For purposes of the present invention, the "trunk" of a human is the body of a human excluding the head, neck and limbs.

The serotonin agonist for use in the present invention, includes for example and without limitation, sumatriptan, naratriptan, eletriptan, rizatriptan, zolmitriptan, almotriptan, frovatriptan, pharmaceutically acceptable salts thereof, mixtures thereof, and derivatives thereof. Preferably the serotonin agonist is sumatriptan (3-(2-(dimethylamino)ethyl)-N-methyl-1H-indole-5-methanesulfonamide), one of its salts or derivatives. As used herein, the identification of an agent to be delivered includes not only the serotonin agonist per se but also its topically administrable prodrugs, active metabolites and prodrugs of the active metabolites.

Every triptan has a basic indole ring, but their side chains differ. These side chains affect the pharmacokinetics of these agents in ways that may be clinically significant and which may make them more or less effective transdermally.

Sumatriptan, the first available drug in this class of triptans, is a short-acting triptan with a rapid onset. It is available in three dosage forms; in the order of decreasing speed of onset of action, these are: subcutaneous injection, nasal spray, and oral tablet. The second triptan on the market was zolmitriptan, which has better bioavailability than sumatriptan, but is otherwise quite similar in clinical use. Zolmitriptan is available in an oral tablet formulation. Zolmitriptan, unlike sumatriptan does cross an intact blood-brain barrier, but the clinical relevance of this is unclear. The third available triptan was rizatriptan which has a rapid onset of action and is available in a conventional oral tablet formulation and also in a rapid-dissolving disc formulation, called MLT. MLT disc rapidly dissolves in the mouth without water. The fourth available triptan was naratriptan, which is distinctive in having a slower onset of action and a longer half-life than other triptans.

Comparative oral doses of certain triptans are as follows: sumatriptan, 50 mg; rizatriptan, 10 mg; naratriptan, 2.5 mg; zolmitriptan, 2.5 mg; and eletriptan, 40 to 80 mg. Therefore, one skilled in the art can readily determine therapeutically equivalent doses of serotonin agonists that may be useful in the present invention. However, it is noted that the differences in oral doses may not directly correspond to the differences in doses that are therapeutically effective via transdermal delivery of the serotonin agonist. Factors such as metabolism of the serotonin agonist, the ability of the drug to pass through the skin, among others, may affect the amount of serotonin agonist necessary to provide a therapeutic effect. One skilled in the art would readily understand this and adjust for the same.

The synthesis of certain serotonin agonists of the present invention can be carried out according to British Patents No. 2 124 210 B and 2 162 522 B; EP-0 500 086 A; EP-A-303 507; U.S. Pat. No. 4,997,841; EP-A-592 438; U.S. Pat. No. 5,545, 644; WO 9206973; EP-A-486 666; EP-A-636 623; U.S. Pat. No. 5,399,574; 5,466,699; WO 91/18897, the disclosures of which are hereby incorporated by reference.

In certain preferred embodiments, the methods of the present invention further include a method of treating a human patient suffering from migraine or cluster headache comprising applying a topical formulation, or transdermal therapeutic system, comprising sumatriptan, a pharmaceutically acceptable salt thereof, or derivative thereof, to the headache region of the patient, the topical formulation providing a serum level of sumatriptan from about 5 ng/ml to about 110 ng/ml, preferably from about 10 ng/ml to about 80 ng/ml. In certain embodiments, the method provides a serum level of sumatriptan from about 50 ng/ml to about 70 ng/ml.

In certain embodiments of the present invention, the serotonin agonist is in an amount of from about 0.5 mg to about 200 mg, preferably the serotonin agonist is in an amount of from about 0.5 mg to about 100 mg, and most preferably from about 10 mg to about 100 mg.

In certain preferred embodiments, the formulations of the present invention contain sumatriptan base or a pharmaceutically acceptable salt thereof (e.g., sumatriptan succinate) as the serotonin agonist. When the serotonin agonist is sumatriptan or a pharmaceutically acceptable salt thereof, the amount of sumatriptan is in an amount of from about 0.5 mg to about 200 mg, preferably in an amount of from about 5 mg to about 200 mg, from about 5 mg to about 100 mg, from about 5 mg to about 50 mg, or from about 5 mg to about 25 mg, and most preferably is in an amount of 12.5 mg, 25 mg, 50 mg or 100 mg.

The amount that constitutes a therapeutically effective amount may vary according to any drugs being coadministered with the serotonin agonist, desired duration of treatment, the surface area of the skin over which the formulation or device is to be placed, and other components of the formulation or device. Accordingly it is not practical to enumerate particular preferred amounts but such can be readily determined by those skilled in the art with due consideration of these factors. Generally, however, when the serotonin agonist is present in a device of the invention, the serotonin agonist is present in an amount by weight of about 1 to about 25 percent, preferably about 5 to 15 percent, by weight based on the total weight of the adhesive layer.

In certain embodiments of the present invention, the serotonin agonist is in a topical administration form (e.g., a topical formulation) of an ointment, cream, lotion, paste, gel, or the like.

A topical formulation containing a serotonin-agonist in accordance with this invention may be used to treat any condition capable of treatment with serotonin agonists, e.g., migraine headaches and cluster headaches. The topical formulation can be placed on the skin of the headache region and allowed to remain for a time sufficient to achieve or maintain the intended therapeutic effect.

The topical formulations of the present invention (e.g., ointment, gel, cream, or the like), must be suitable for topical administration of a drug, i.e., must contain pharmaceutically acceptable excipients compatible with application to the skin tissue, and may optionally contain a sufficient amount of an enhancer composition as described hereinafter.

In certain embodiments, in addition to the serotonin agonist, the topical formulations and/or transdermal therapeutic systems of the present invention may include at least one adjuvant such as a penetration enhancer, anti-oxidant, stabilizer, carrier, or vehicle. Additionally or alternatively, the present invention may include the application of electric current (iontophoresis) for enhancing permeation of the serotonin agonist.

In certain embodiments of the present invention, wherein the topical formulation further includes a penetration enhancer composition, the amount of enhancer composition present in the formulation will depend on a number of factors, e.g., the strength of the particular enhancer composition, the desired increase in skin permeability, and the amount of drug which is necessary to deliver.

In certain embodiments, the topical formulations comprising a serotonin agonist in an ointment, gel, cream or the like, will typically contain on the order of about 0.001 to about 80% by weight, preferably 0.01 wt. % to 50 wt. % serotonin agonist, and about 0 wt. % to about 50.0 wt. %, preferably from about 1 wt. % to about 30 wt. % of a permeation enhancer composition, with the remainder of the composition comprising a carrier or vehicle.

Suitable enhancers include, but are not limited to, dimethylsulfoxide (DMSO), N,N-dimethylacetamide (DMA), decylmethylsulfoxide ($C_{10}$ MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil.

Additional enhancers for use in conjunction with the present invention are lipophilic compounds having the formula $[RCOO]_nR'$, wherein n is 1 or 2 and R is $C_1$-$C_{16}$ alkyl optionally substituted with 1 or 2 hydroxyl groups, and R' is hydrogen or $C_1$-$C_{16}$ alkyl optionally substituted with 1 or 2 hydroxyl groups. Within this group, a first subset of compounds are represented by the formula $[CH_3(CH_2)_mCOO]_nR'$ in which m is an integer in the range of 8 to 16, n is 1 or 2, and R' is a lower alkyl ($C_1$-$C_3$) residue that is either unsubstituted or substituted with one or two hydroxyl groups. Preferred enhancers within this group include an ester which is a lower alkyl ($C_1$-$C_3$) laurate (i.e., m is 10 and n is 1) such as "PGML". It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula $CH_3(CH_2)_m$—O—CO—$CHR_1R_2$, in which $R_1$ and $R_2$ are independently hydrogen, hydroxyl, or lower alkyl ($C_1$-$C_3$), and m is as above. Particularly preferred enhancers within this group are lauryl lactate and myristyl lactate. In addition, a third subset of compounds within this group are analogous fatty acids, i.e., acids having the structural formula $CH_3(CH_2)_m COOH$ where m is as above. A particularly preferred acid is lauric acid.

Other enhancer compositions are wherein a lipophilic compound as just described, particularly PGML is combined with a hydrophilic compound, such as a $C_2$-$C_6$ alkanediol. One preferred hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol®) and diethylene glycol monomethyl ether. Such enhancer compositions are described in detail in U.S. Pat. Nos. 5,053,227 and 5,059,426 to Chiang et al., the disclosures of which are herein incorporated by reference.

Other enhancer compositions may include mixture or combinations of any of the aforementioned enhancers, and the like.

In certain embodiments the topical formulation may include at least one water-insoluble, pharmacologically approved, alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

In certain embodiments, the topical formulation may further include hydrocarbons such as liquid paraffin, vaseline, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

In certain embodiments, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain embodiments of the present invention, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like.

In certain embodiments of the present invention, it has been found that the percentage of patients experiencing migraine or cluster headache pain relief may be significantly improved based on an aqueous based topical formulation as demonstrated by the appended examples. Some examples of patents disclosing pharmaceutical compositions which rely upon an aqueous gel composition as a vehicle for the application of a drug are U.S. Pat. Nos. 4,883,660; 4,767,619; 4,511,563; 4,861,760; and 5,318,780, the disclosures of which are herein incorporated by reference.

The topical formulation may further include one or more preservatives, stabilizers, or anti-oxidants.

Examples of preservatives that may be used in a formulation according to the present invention include, but are not limited to, bacteriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agents, chelating agents and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other adjuvants that may be included in the drug formulation include carriers, tackifiers, pigments, dyes, and other additives that do not adversely affect the mechanical or adhesive properties of the formulation.

"Carriers" or "vehicles" as used herein refer to carrier materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "carrier" or "vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

Carrier materials suitable for use in the instant compositions include those well-known for use in the cosmetic and medical arts as bases for ointments, lotions, salves, aerosols, suppositories and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers herein include for example alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

In certain embodiments of the present invention, the formulations of the present invention may be formulated as a transdermal delivery system (also referred to herein as a transdermal therapeutic system) such as a transdermal patch, a transdermal plaster, a transdermal disc, iontophoretic transdermal device, or the like.

In certain embodiments, the serotonin-agonist containing transdermal delivery devices, as well as other transdermal delivery systems in accordance with the invention can be made in the form of an article such as a tape, a patch, a sheet, a dressing or any other form known to those skilled in the art. Generally the device will be in the form of a patch of a size suitable to deliver a unit dose of serotonin agonist through the skin. The serotonin agonist may be introduced into a transdermal therapeutic system in different forms (solid, in solution, in dispersion); it may also be microencapsulated.

In certain embodiments the present invention provides a transdermal therapeutic system comprising a serotonin agonist in an amount that would provide sub-therapeutic plasma levels if administered orally, but is therapeutically effective when administered via transdermal delivery at the headache region.

A transdermal delivery system for use in accordance with the present invention can also be constructed with an enhancer composition and other ingredients described hereinabove with respect to the topical formulation. Preferably the transdermal delivery system is formulated for the rapid delivery of a serotonin agonist as would be beneficial to a person suffering from a migraine or a cluster headache. The targeted skin flux for delivery of a particular drug can be achieved by adjusting vehicle composition and vehicle loading, as well as by adjusting the surface area through which the compositions are administered to skin.

The transdermal delivery system used in the present invention may be prepared, for example, in accordance with U.S. Pat. Nos. 5,069,909; 4,806,341; 5,026,556; 4,588,580; 5,016,652; 3,598,122; 4,144,317; 4,201,211; 4,262,003; and 4,379,454; all of which are incorporated herein by reference.

In certain embodiments of the present invention, wherein the transdermal delivery system is a transdermal patch, the transdermal patch comprises a serotonin agonist contained in a reservoir or a matrix, and an adhesive which allows the transdermal patch to adhere to the skin, allowing the passage of the active agent from the transdermal patch through the skin of the patient. Once the serotonin agonist has penetrated the skin layer, the drug is absorbed into the blood stream where it exerts the desired pharmaceutical effects.

In certain embodiments, the dosage form can be a transdermal patch comprising a laminated composite for administering said serotonin agonist to an individual transdermally comprising: (a) a polymer backing layer that is substantially impermeable to said serotonin agonist; and (b) a reservoir layer comprising a water-base acrylate pressure-sensitive adhesive, 1 to 12% by weight serotonin agonist and 2 to 25% by weight of a permeation enhancer comprising propylene glycol monolaurate in combination with capric acid or oleic acid, wherein the skin contact area of the composite is 10 to 100 cm$^2$.

The dosage form can be a transdermal patch comprising (a) a polar solvent material selected from the group consisting of $C_3$-$C_4$ diols, $C_3$-$C_6$ triols, and mixtures thereof; and (b) a polar lipid material selected from the group consisting of fatty alcohol esters, fatty acid esters, and mixtures thereof; wherein said polar solvent material and said polar lipid material are present in a weight ratio of solvent material:lipid material of from about 60:40 to about 99:1.

In certain embodiments, the dosage form also comprises a transdermal plaster comprising: a film layer which comprises a polyester film of 0.5 to 4.9 μm thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which (a) the average particle size is 0.001 to 3.0 μm, and (b) the average particle size is substantially not more than 1.5 times the thickness of said polyester film; and an adhesive layer (a) which is composed of an adhesive containing said serotonin agonist and further wherein said adhesive layer (a) is laminated on said film layer over the surface in a 2 to 60 μm thickness.

In certain embodiments, the dosage form can be a transdermal disc comprising: (a) a backing layer which is substantially impervious to said serotonin agonist; and (b) a polymer matrix disc layer which is adhered to said backing layer and which has microdispersed therein said serotonin agonist, said polymer being bioacceptable and permitting said serotonin agonist to be transmitted for transdermal absorption, said serotonin agonist being stable in said polymer matrix.

In certain preferred embodiments, the treatment of the migraine and/or cluster headache is by application of the transdermal therapeutic system (e.g., patch) comprising the serotonin agonist to the headache region.

In certain embodiments, the present invention further provides for applying a topical formulation as described herein for the immediate release of the serotonin agonist upon an acute attack, plus the application of a transdermal therapeutic system (e.g., a patch) for the prophylactic treatment of secondary attacks due to the delayed effect of the transdermal therapeutic system.

In certain embodiments, in addition to the serotonin agonist, the topical formulation or transdermal therapeutic system may further comprise another active ingredient in combination with the serotonin agonist, e.g., analgesics, antimimetics, psychopharmacologic agents, or sedatives.

The present invention is contemplated to encompass all transdermal formulations, e.g., the technologies described above, with the inclusion of a serotonin agonist, such that the administration of the serotonin agonist provides for the relief of migraine and/or cluster headaches.

In certain embodiments, the present invention further provides for a method of manufacturing the formulations of the present invention comprising grinding the serotonin agonist (e.g., sumatriptan succinate) into fine particles; mixing the particles with a aqueous and/or organic solution to provide for a solution or dispersion of the serotonin agonist; filtering and rinsing the residue; preferably bringing the volume of the filtrate to that of the final product; preferably concentrating the filtrate (preferably using a low pressure vacuum) to 25% of the original volume; mixing the condensed filtrate with a requisite amount of a carrier (e.g., Lipoderm®); and preferably placing the final formulation in a metered dosing device (or alternatively, otherwise dividing the formulation into unit doses prior to use).

The present invention will now be more fully described with reference to the accompanying examples. It should be understood, however, that the following description is illustrative only and should not be taken in any way as a restriction on the generality of the invention specified above.

EXAMPLE 1

Transdermal Gel

A sumatriptan gel was produced with the formula set forth in Table 1 below:

TABLE 1

| Ingredient | Amt/unit (mg) |
| --- | --- |
| Imitrex ® (sumatriptan succinate) 100 mg tablet | 2200 mg (22 tablets) |
| Ethoxy Diglycol Liquid | 2.200 gm |
| Lecithin/Isopropyl Palmitate 50/50 gel | 4.400 gm |
| Pluronic F127 20% Liquid | 11.286 gm |

Dosage forms of the above formulation were prepared according to the following procedure:
1. 100 mg Imitrex® tablets (sumatriptan succinate) are crushed and mixed with Lecithin/Isopropyl Palmitate 50/50 gel.
2. Thereafter, the Ethoxy diglycol liquid is added and mixed together with 1.
3. The pluronic F127 20% is also added to the mixture.
4. The resultant formulation is put through an ointment mill and 1 ml unit doses are placed in 1 ml oral syringes. The syringes contain a gel having a sumatriptan concentration of 100 mg/ml.

EXAMPLE 2

Drug Study Using Formulation of Example 1

An open study was conducted where physician, pharmacist and patient were aware of the medication being used and aware of the expected results. Two written surveys were sent to each patient and a telephone call was placed to those who did not respond to the written survey.

In the study, 43 patients were each given a single 1 ml oral syringe containing 100 mg/ml of a transdermal sumatripan formulation prepared in accordance with Example 1. Patients were instructed initially to apply 0.25 ml (containing 25 mg sumatriptan) to the temples at the onset of the aura of a migraine or at the onset of a migraine (whichever occurred to them). Patients were also told to apply to the base of the neck if necessary. Four Band-Aids were dispensed with each prescription and the patients were told to apply the patch over the transdermal sumatriptan. If a 25 mg dose was not sufficient, the patients were told they could reapply a second 25 mg dose in 2 hours after the initial dose. Patients were told to wash their hands after application.
  A. A telephone survey was conducted which gave the following results:
    2 of 29 patients preferred injectable sumatriptan;
    2 of 29 patients preferred nasal sumatriptan;
    9 of 29 patients were unable to be reached;
    4 of 29 patients reported transdermal sumatriptan did not work;
    6 of 29 patients did not use the transdermal sumatriptan as of the telephone survey; and
    6 of 29 patients reported that transdermal sumatriptan worked well.
  B. Of the written surveys, fourteen were returned, which gave the following results:
  1. With respect to time to pain relief:
    3 of 14 patients had pain relief within 10 to 15 minutes;
    3 of 14 patients had pain relief within 30 minutes;
    2 of 14 patients had pain relief within 60 minutes;
    1 of 14 patients had pain relief in about 120 minutes;
    1 of 14 patients had pain relief in longer than 120 minutes;
    3 of 14 patients did not get relief from transdermal sumatriptan; and
    1 of 14 patients did not "really" get relief (however, via telephone survey, patient said did get relief).
  2. With respect to recurrence:
    2 of 14 patients had no reoccurrence;
    2 of 14 patients had reoccurrence within 1 hour;
    3 of 14 patients had reoccurrence within 4 hours;
    1 of 14 patients had reoccurrence within 24 hours;
    6 of 14 patients did not answer the question; and
    1 of 14 patients did not get initial relief, therefore reoccurrence was not applicable.
  3. With respect to the requirement of a second dose:
    3 of 14 patients were unable to answer the question;
    8 of 14 patients did apply a second dose; and
    3 of 14 patients did not apply a second dose.
  4. With respect to pain relief if a second dose was applied:
    4 of 8 patients did not get further pain relief; and
    4 of 8 patients did not get relief with 50 mg total dose at that point.
  5. With respect to whether patients had to use another dosage form to obtain relief:
    5 of 14 patients did not have to use any other dosage form to get relief;
    3 of 14 patients used nasal as an alternate route;
    1 of 14 patients used injectable as an alternate route;
    3 of 14 patients used oral as an alternate route; and
    2 of 14 patients did not answer the question.

EXAMPLE 3

Drug Study Using Formulation of Example 1

The efficacy of topical sumatriptan was studied over a six-week period in 22 migraineurs currently treated with injectable, nasal spray or oral sumatriptan. The migraine frequency of the migraineurs for which triptan therapy was used ranged from 1 to greater than 4 per week. Use of the presently marketed triptan formulations had been established in some of the patients for years. The purpose of the study was to determine the effectiveness and convenience of topical sumatriptan in comparison to previous formulations.

In the study, 22 patients were each given a single 1 ml oral syringe containing 100 mg/ml of a transdermal sumatripan formulation prepared in accordance with Example 1. Patients were instructed initially to apply 0.5 ml (containing 50 mg sumatriptan) to the side of the forehead where the patient is experiencing their headache at a time that they would usually resort to using sumatriptan for relief. The patients were told that an additional 0.5 ml (containing 50 mg sumatriptan) could be applied if the first dose was ineffective, one hour after the initial dose. Application of the topical sumatriptan took about 3 to 5 seconds by placing it on the finger and rubbing the forehead several times.

The following are results of the eleven patients who responded to the surveys conducted:
  A. 6 out of 11 patients (55%) reported that transdermal sumatriptan relieved their headache.
  B. 4 out of 11 patients (36%) reported a preference for the transdermal route over other routes, giving the following reasons:
    1. 3 of the 4 patients indicated because it worked quickly;
    2. 4 of the 4 patients indicated because it was more convenient; and
    3. 3 of the 4 patients indicated because of the lack of side effects.
  C. 4 out of 11 patients (36%) achieved relief with a single 50 mg dose and indicated the following times to relief:

1. 1 of the 4 patients indicated relief in 10 minutes;
2. 1 of the 4 patients indicated relief in 30 minutes;
3. 1 of the 4 patients indicated relief in 60 to 120 minutes;
4. 1 of the 4 patients did not indicate time to relief.

D. The following results were also indicated by the survey:
1. 2 of the 11 patients indicated a preference for the injectable sumatriptan;
2. 2 of the 11 patients indicate a preference for the nasal spray; and none indicated a specific preference for the pill (oral) form.

EXAMPLE 4

Transdermal Gel

An aqueous based sumatriptan gel was produced with the formula set forth in Table 2 below:

TABLE 2

| Ingredient | Amt/unit (mg) |
|---|---|
| Imitrex ® (sumatriptan succinate) 100 mg tablet | 2200 mg (22 tablets) |
| Lipoderm ®/LIP* | q.s. |

*Lipoderm ®/LIP is a commercially marketed compounding agent having the following ingredients: Ethoxydiglycol, Water (Aqua), Glycerin, $C_{12-15}$Alkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, *Aloe Vera (Aloe Barbadensis)*, Tocopheryl Acetate (Vitamin E Acetate), *Prunus Amygadalus Amara* (Bitter Almond) Kernel Oil, *Vitis Vinifera* (Grape) Seed Extract, *Triticum Vulgare* (Wheat) Germ Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate.

Dosage forms of the above formulation in Table 2 were prepared according to the following procedure:
1. 100 mg Imitrex® tablets (sumatriptan succinate) are crushed and mixed with a sufficient amount of Lipoderm® to provide a sumatriptan concentration of 100 mg/ml.
2. The resultant formulation is put through an ointment mill and 1 ml unit doses are placed in 1 ml oral syringes. The syringes contain a gel having a sumatriptan concentration of 100 mg/ml.

EXAMPLE 5

Drug Study Using Formulation of Example 4

The efficacy of the topical sumatriptan prepared in accordance with Example 4 was studied in 10 migraineurs currently treated with injectable, nasal spray or oral sumatriptan.

In the study, 10 patients were each given a single 1 ml oral syringe containing 100 mg/ml of a transdermal sumatripan formulation of Example 4. Patients were instructed initially to apply 0.5 ml (containing 50 mg sumatriptan) to the side of the forehead where the patient is experiencing their headache and 0.5 ml (containing 50 mg sumatriptan) over the posterior cervical area (back-of-the-neck region) on the same side of the headache at a time that they would usually resort to using sumatriptan for relief. If the headache was bilateral, the patients were instructed to apply one-half of the 100 mg (0.5 ml) to each side at a time that they would usually resort to using sumatriptan for relief. The patients were instructed to "prep" the skin with an alcohol swab prior to the application of the gel to rid the area of dirt, makeup, oil, etc.

The following are results of the ten patients:
1. There was a greater than 80% headache relief rate as opposed to the 55% with the oil based formula of example 1.
2. There was improved time to headache relief in comparison to the oil based formula of example 1.
3. Relief was apparent in most patients by 10 to 15 minutes, and complete by 30 to 45 minutes post application.
4. The aqueous gel was more easily applied than the oil-based formula and left little or no residue, which could easily be wiped away with a wet cloth.
5. The initial 100 mg dose was more effective than the previous 50 mg applied in example 3 and was well tolerated and without significant side effects. There was only an occasional noting of "a tingling sensation" of the scalp at the site of application.
6. The first indication of relief expressed by patients was that of the frontotemporal scalp and neck muscles "loosening up." This was followed by the sensation of "the head feeling lighter" with eventual relief of throbbing head pain. Similar symptoms have been expressed by patients habitually using sumatriptan injection for migraine headaches.

EXAMPLE 6

Drug Study Using Formulation of Example 4

30 established migraineurs were treated with 100 mg of transdermal sumatriptan as prepared in Example 4 for acute moderate-to-severe attacks. Some patients used the transdermal sumatriptan formulation on multiple occasions. After cleansing with an alcohol swab, the sumatriptan formulation (100 mg/ml) was applied to the posterior cervical area in close proximity to the brainstem, the site of migraine pathology, i.e., "migraine generator".

Each patient was requested to answer a questionnaire after using the topical formulation. With respect to the written questionnaires the patients responded as follows:
1. With respect to the symptoms that the patient experienced during the migraine attack:
   23 of the patients experienced nausea.
   9 of the patients experienced vomiting.
   26 of the patients experienced light sensitivity.
   16 of the patients experienced sensitivity to sound.
   18 of the patients experienced neck pain.
   11 of the patients experienced facial pain.
   30 of the patients experienced throbbing headache.
   15 of the patients experienced dizziness/lightheadedness.
   6 of the patients experienced confusion.
   Other: difficulty breathing and shortness of breath (1); syncope (1); insomnia (1); tinnitus (1); anorexia (1); blurred vision (3); sweats (1); cold and clammy (1); neck tightness (3); tightness behind eyes (1); shoulder tightness (1); lethargy (1); sinus pressure (3); scalp sensitivity (1); diarrhea (1); and arm pain (1); sinus congestion (1).
2. With respect to when the patient first experienced relief of any migraine symptom(s) (outside of pain relief)*:
   Total patients listed is 32 because two of the thirty patients indicated different times with respect to different occasions of using the topical formulation.
   15 first experienced relief in less than 5 minutes.
   15 first experienced relief in 5 minutes to 15 minutes.
   2 first experienced relief 16 minutes to 30 minutes.
   none first experienced relief greater than 30 minutes.
3. With respect to when the patient experienced initial relief of pain*:
   Total patients listed is 34 because four of the thirty patients indicated different times with respect to different occasions of use.
   7 experienced initial relief of pain in less than 5 minutes.

21 experienced initial relief of pain in 5 minutes to 15 minutes.

5 experienced initial relief of pain in 16 minutes to 30 minutes.

1 experienced initial relief of pain in greater than 30 minutes.

4. With respect to when the patient experienced complete pain relief (pain free)*:

Total patients listed is 34 because three of the thirty patients indicated different times with respect to different occasions of use (2 patients indicating 2 different times and 1 patient indicating 3 different times).

9 experienced complete pain relief in less than 15 minutes.

9 experienced complete pain relief 16 minutes to 30 minutes.

6 experienced complete pain relief in 31 minutes to 45 minutes.

3 experienced complete pain relief in 46 minutes to 60 minutes.

3 experienced complete pain relief in 61 minutes to 90 minutes.

3 experienced complete pain relief in 91 minutes to 120 minutes.

1 experienced complete pain relief in greater than 120 minutes.

5. With respect to when the patient experienced relief of ALL of the patient's migraine symptoms*:

Total patients listed is 32 because two of the thirty patients indicated different times with respect to different occasions of use 5 experienced relief of all migraine symptoms in less than 15 minutes.

10 experienced relief of all migraine symptoms in 16 minutes to 30 minutes.

7 experienced relief of all migraine symptoms in 31 minutes to 45 minutes.

3 experienced relief of all migraine symptoms in 46 minutes to 60 minutes.

3 experienced relief of all migraine symptoms in 61 minutes to 90 minutes.

3 experienced relief of all migraine symptoms in 91 minutes to 120 minutes.

1 experienced relief of all migraine symptoms in greater than 120 minutes.

6. With respect to if the patient experienced recurrence of the headache pain within 24 hours:

28 of the patients said that they did not have a recurrence within 24 hours.

2 of the patients said that they did have a recurrence within 24 hours.

7. With respect to whether the patient experienced any side effects using transdermal sumatriptan:

25 of the patients said that they did not experience any side effects.

Of the 5 patients experiencing side effects, side effects listed were as follows:

Tingling and warmth at application site (1); tingling neck and left hand (1);

Tingling of skin at application site (1); burning sensation in scalp (1); slight tingling of skin and "warm" feeling (1).

8. With respect to other forms of migraine medications the patient has used in the past:

30 of the patients said they have used a tablet formulation to treat migraine.

2 of the patients said that they have used a melt formulation to treat migraine.

3 of the patients said that they have used a nasal spray formulation to treat migraine.

9 of the patients said that they have used an injection formulation to treat migraine.

9. Comments that the patient had relative to transdermal therapy:

Comments from the patients varied with respect to the formulations. Most notably, patients comments were as follows:

Cost prohibitive (1); worked better and faster than any other treatment she used (used tablet and injection in the past) (1); faster relief (1); worked fast (1); able to use ½ dose transdermal with success (age 8) (1); never experienced anything to work so well or so fast (1); on two occasions patient had taken Imitrex® tablet without benefit, but responded to transdermal (1); transdermal did not cause lethargy that pill caused (1); exclusively uses transdermal for migraines; has used 20 times; also 3 week period of headaches stopped only with transdermal; cream crumbles like any cheese after applied but "I'm not complaining" (1); regular user of transdermal 10-15 times; transdermal is more subtle than pill (1); has used transdermal 6-7 times and works faster than pill; application not convenient and sometimes and pain relief not as long as imitrex pills (1); faster than pills (1); uses regularly (1); worked fast, easy to administer (1); very fast without side effects (1); initial didn't absorb, greasy water based better (absorbed better); and wonderful (1).

10. With respect to whether the patient would use transdermal sumatriptan again to treat another migraine:

All 30 of the patients said they would use transdermal sumatriptan again to treat another migraine.

Typically the first relief symptom expressed by patients using transdermal sumatriptan is the relaxation of cervical musculature, followed by decreased nausea and photophobia and the eventual relief of throbbing head pain. It is believed that with the local application of transdermal sumatriptan, the brainstem and surrounding tissue are concentrated with the drug accounting for its rapid and prolonged clinical effect. The relative paucity of side effects, particularly the typical "triptan effects" may be explained on the basis of minimal system absorption, with much of the drug remaining concentrated near the site of application. In view of the above, the data suggests that the transdermal route is as effective as injection, but without the usual side effects.

As can been seen from the above examples, the percentage of patients experiencing migraine or cluster headache pain relief may be significantly improved using an aqueous based topical formulation. Additionally, the percentage of patients experiencing migraine or cluster headache pain relief may be significantly improved without a significant increase in side effects using an increased dose as demonstrated by the above examples.

EXAMPLE 7

A sumatriptan formulation having a final strength of 12.5 mg/0.1 ml was prepared according to the following procedure:

1. Triturate the requisite amount of sumatriptan succinate tablets in a mortar and pestle to a small particle size.
2. Wet the powder with 95% ethyl alcohol and triturate. Add pure water and triturate again.
3. Filter and rinse the residue twice with enough water to bring the volume of the filtrate to that of the final product. For example, if preparing 100 ml of the transdermal migraine formulation, filter until the total volume of the filtrate reaches 100 ml.

4. Concentrate the filtrate using low pressure vacuum to 25% of the original volume (e.g., to 25 ml in the example).
5. Mix the condensed filtrate and Lipoderm® in mixing syringes to the desired volume (e.g., 100 ml in step 3). The final strength is 12.5 mg of sumatriptan succinate per 0.1 ml.

EXAMPLE 8

12 migraineurs (patient 8 was treated on two occasions) were each treated with 12.5 mg of sumatriptan of the formulation prepared in accordance with Example 7. The patients were told to clean the back of the neck with an alcohol swab and dry with a clean tissue before application. The patients were told withdraw 12.5 mg (0.1 ml) of the transdermal sumatriptan gel contained in a calibrated 1 ml syringe for metered administration, and apply 12.5 mg of the transdermal sumatriptan gel by gently rubbing the gel into the skin on the back of the neck at the onset of headache and repeating in one-half hour if migraine persists. The following table lists the results.

TABLE 4

| Patient # | Age in years | Sex | Years with migraine | Initial relief of headache and migraine symptoms (minutes) | Complete pain relief (minutes) |
|---|---|---|---|---|---|
| 1 | 50 | F | >20 | 1 | 10 |
| 2 | 42 | F | 16 | 2-3 | 10-12 |
| 3 | 47 | F | 20 | 3 | 25 (12.5 mg reapplied after recurrence with subsequent complete relief) |
| 4 | 45 | F | 11 | 2 | 15-20 |
| 5 | 52 | F | >30 | 3-5 | 15 |
| 6 | 37 | F | 11 | 2 | 15-20 |
| 7 | 17 | F | 1 | 3-5 | 20-25 |
| 8(a) | 17 | F | 1½ | 1 | 8 |
| 8(b) | | | | 2 | 20 |
| 9 | 36 | F | 20 | 2 | 30 |
| 10 | 37 | F | 23 | 3 | 15 |
| 11 | 66 | F | 2 years with muscle contraction headaches | 2 | 15 |
| 12 | 55 | F | 8 years with muscle contraction headaches after auto accident | 8-10 | 30-45 |

Many other variations of the present invention will be apparent to those skilled in the art and are meant to be within the scope of the claims appended hereto.

What is claimed is:

1. A method for treating a migraine or cluster headache comprising:
applying a topical formulation containing an effective amount of sumatriptan or a pharmaceutically acceptable salt thereof topically to the skin at the posterior cervical area of a human patient in close proximity to the brain stem, the topical formulation comprising the sumatriptan in an immediate release topical vehicle and providing rapid delivery of the sumatriptan for immediate absorption at the posterior cervical area of the human patient, to provide relief of a migraine or cluster headache which is occurring or is imminent in the patient.

2. The method of claim 1, further comprising preparing the topical formulation as a preparation selected from the group consisting of a cream, gel, lotion, emulsion, viscous liquid, and foam.

3. The method of claim 2, further comprising preparing the topical formulation in an aqueous based vehicle.

4. The method of claim 3, wherein said sumatriptan is in a topical formulation selected from the group consisting of a cream, gel, lotion, emulsion, viscous liquid, and foam.

5. The method of claim 1, wherein the patient experiences relief of the migraine or cluster headache within about 2 hours after applying the topical formulation.

6. The method of claim 1, wherein said amount of said sumatriptan is in an amount of from about 0.5 mg to about 200 mg.

7. The method of claim 1, wherein a unit dose of the topical formulation containing sumatriptan or a pharmaceutically acceptable salt thereof comprises from about 0.5 to about 200 mg of sumatriptan, by weight based on the succinate salt of sumatriptan, said unit dose providing relief from a migraine or cluster headache within about 2 hours after topical administration to said human patient.

8. The method of claim 1, further comprising applying a second application of said sumatriptan to the same or different headache region within about 2 hours after applying the first application.

9. The method of claim 1, further comprising applying the formulation to an area of intact skin in the range of about 20 $cm^2$ to about 60 $cm^2$.

10. The method of claim 1, further comprising reducing the side effects of said sumatriptan as compared to oral administration of said sumatriptan by applying the formulation to the posterior cervical area.

11. A method for treating a migraine or cluster headache comprising:
applying a dose of a topical formulation containing an effective amount of sumatriptan or a pharmaceutically acceptable salt thereof topically to the skin at the posterior cervical area of a human patient in close proximity to the brain stem, the topical formulation comprising the sumatriptan in an aqueous based immediate release topical vehicle and providing rapid delivery of the sumatriptan for immediate absorption at the posterior cervical area of the human patient, to provide relief of a migraine or cluster headache which is occurring or is imminent in said patient, the dose of the sumatriptan comprising from about 0.5 to about 200 mg of sumatriptan, by weight based on the succinate salt of sumatriptan, wherein the dose provides relief from a migraine or cluster headache within about 2 hours after topical administration to the human patient.

12. The method of claim 11, wherein said sumatriptan is in a topical formulation selected from the group consisting of cream, gel, lotion, emulsion, viscous liquid, and foam.

13. The method of claim 11, further comprising reducing the side effects of the sumatriptan as compared to oral administration of the sumatriptan by applying the formulation to the posterior cervical area.

14. The method of claim 11, further comprising providing the dose of the sumatriptan in a metered dose device containing multiple unit doses of the sumatriptan.

15. The method of claim 11, wherein the sumatriptan is selected from the group consisting of sumatriptan base, sumatriptan succinate, and mixtures thereof.

16. The method of claim 11, wherein the patient experiences pain relief within less than about 30 minutes after application of the dose.

17. A method for treating a migraine or cluster headache comprising:

topically applying a dose of a topical aqueous based immediate release formulation containing from about 0.5 to about 200 mg of sumatriptan, by weight based on the succinate salt of sumatriptan, to the skin at the posterior cervical area of a human patient in close proximity to the brain stem, to provide rapid delivery of the sumatriptan for immediate absorption at the posterior cervical area of the human patient such that the dose provides relief from a migraine or cluster headache within about 2 hours after topical administration to the human patient, the topical formulation selected from the group consisting of cream, gel, lotion, emulsion, viscous liquid, and foam.

* * * * *